(12) United States Patent
Kristen et al.

(10) Patent No.: US 6,812,306 B2
(45) Date of Patent: Nov. 2, 2004

(54) METALLIC COMPOUNDS AND THE USE THEREOF IN THE POLYMERIZATION OF OLEFINS

(75) Inventors: Marc Oliver Kristen, Limburgerhof (DE); Peter Hofmann, Heidelberg (DE); Frank Eisenträger, Bornheim-Walberberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/312,880

(22) PCT Filed: Jul. 4, 2001

(86) PCT No.: PCT/EP01/07640

§ 371 (c)(1),
(2), (4) Date: Jan. 2, 2003

(87) PCT Pub. No.: WO02/02573

PCT Pub. Date: Jan. 10, 2002

(65) Prior Publication Data

US 2003/0187161 A1 Oct. 2, 2003

(30) Foreign Application Priority Data

Jul. 6, 2000 (DE) .......................... 100 32 403

(51) Int. Cl.$^7$ .............................. C08F 4/80; C08F 4/82; C07F 15/04
(52) U.S. Cl. .................... 526/169.1; 526/161; 526/172; 502/155; 502/213; 556/13; 556/18; 556/19; 556/22; 556/138; 556/140; 556/137
(58) Field of Search .............................. 556/18, 19, 13, 556/22, 137, 138, 140, 136; 526/161, 172, 169.1, 169.2; 502/155, 213

(56) References Cited

U.S. PATENT DOCUMENTS 6,031,057 A    2/2000  Lippert et al.

FOREIGN PATENT DOCUMENTS

| DE | 4134772 A | 10/1990 |
|---|---|---|
| EP | 0 426 638 | 5/1991 |
| EP | 0 468 537 | 1/1992 |
| WO | 96/23010 | 8/1996 |
| WO | 96 37522 | 11/1996 |

OTHER PUBLICATIONS

Bonnet et al., J. Chem. Soc. Chem. Commun. 1994, pp. 615–616.*

Ridgwell et al., J. Chem. Soc. Dalton Trans. 1982, pp. 999–1004.*

Sanshiro, K., Synthesis of Organometallic Compounds 1997, pp. 278–285.*

Michel C., Bonnet et al.: "Synthesis of cationic and neutral methallyl nickel complexes and applications in ethene oligomerization" J. Chem. Soc., Chem. Commun., No. 5, pp. 615–616 1994.

K.N. Issleib et al.: "Complex chemistry of phosphines and phosphine oxides. XXI. Complexing behavior of methylene(diphenyl)phosphine and lithium bis(diphenylphosphino)methanide" Z. Anorg. Chem., vol. 368, No. 1, pp. 89–96 1972.

Philip J. Ridgwell et al.: "Sunthesis and characterization by spectroscopy and x-ray structure determination of palladium complexes containing the 1–2–.eta.1, 2–di–tert–butyl–3–methl–4methylenecyclobutenyl ligand" J. Chem. Soc., Dalton Trans., No. 5, pp. 999–1004 1982.

Stephen Fallis et al.: "Synthesis and reactions of cationic palladium and platinum cyclopentadienyl complexes. Molecular structure of (.eta.5–cyclopentadienyl)'1,2–bis(diphenylphosphino)ethane!platinum(II) triflate" Organometallics, vol. 12, No. 10, pp. 3851–3855 1993.

Komiya Sanshiro: "Synthesis of organometallic compounds" John Wiley & Sons Ltd, Chichester 1997.

Hans–Herbert Brintzinger et al.; "Stereospezlfische olefinpolymerisation mit chiraten matallocenkatalysatoren" Chemistry A European Journal, vol. 1, No. 2, pp. 1255–1283 May 1995.

Houben–Weyl Methoden Der Organischen Chemie, Thiem Verlag Stuttgart vols. 13/1 and 13/2a, pp. 92–102 and 134–159 1970.

Organikum Organisch–Chemisches Grundpraktikum 1984, pp. 784–808.

(List continued on next page.)

Primary Examiner—Roberto Rabago
(74) Attorney, Agent, or Firm—Oblon, Spivak, McClelland, Maier & Neustadt, P.C.

(57) ABSTRACT

Metal compounds of the formula I,

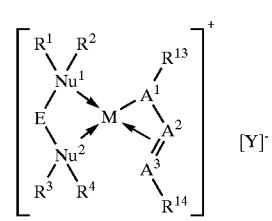

where M is selected from among Ni and Pd in the oxidation state +II can be used for the polymerization or copolymerization of olefins. Supported catalysts for the polymerization and copolymerization of olefins can be obtained by application of one or more of the above-described ionic metal compounds to a support.

16 Claims, No Drawings

OTHER PUBLICATIONS

P. Hoffmann et al. [n$_2$–bis(di–t–butylphosphino)methan)(trans–stilben)nickel(0), Nl(dtbpm)(trans–PhGH=CHPh), Synthese und molekuelstruktur einer vorstufe des 14–elektronenfragments [Ni(dt-bpm)]Z. Naturforsch., vol. 45b, pp. 897–908 1990.

Frederick L. Joslin et al.: "Cyclopentadienyl ruthenium(II) and (III) complexes with a chelating 1,2–bis(dicyclohexylphosphino)methane ligand" Polyhedron, vol. 10, No. 14, pp. 1713–1715 1991.

Joyce S. Yu et al.: "Catalytic hydrogenation of aryl phosphines by niobium aryloxide compounds: high yield and efficient synthesis of cyclohexyl phosphine ligands" J. Chem. Soc., Chem. Commun., pp. 632–633 1992.

M. Brookhart et al.; "[3,5–(CF$_3$)$_2$C$_6$H$_3$)$_4$B]–[H(OEt$_2$)$_2$)]+: A convenient reagent for generation and stabilization of cationic, highly electrophilic organometallic complexes" Organometallics, vol. 11, pp. 3920–3922 1992.

* cited by examiner

METALLIC COMPOUNDS AND THE USE THEREOF IN THE POLYMERIZATION OF OLEFINS

DESCRIPTION

The present invention relates to metal compounds of the formula I,

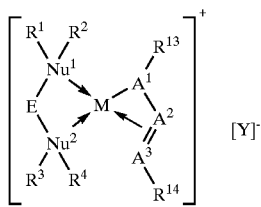

where the variables are defined as follows:

M is selected from among Ni and Pd in the oxidation state +II;

$Nu^1$, $Nu^2$ are selected independently from among N, P and As,

E is selected from among

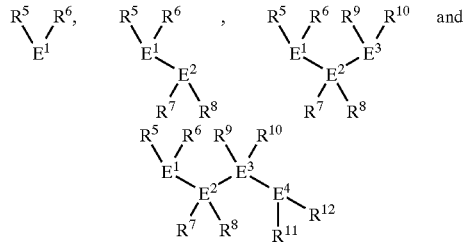

and $E^1$, $E^2$, $E^3$ and $E^4$ are selected independently from among C, Si and Ge;

$R^1$ to $R^{12}$ are selected independently from among
hydrogen,
$C_1$–$C_8$-alkyl, substituted or unsubstituted,
$C_2$–$C_8$-alkenyl, substituted or unsubstituted, having from one to 4 isolated or conjugated double bonds;
$C_3$–$C_{12}$-cycloalkyl, substituted or unsubstituted,
$C_7$–$C_{13}$-aralkyl,
$C_6$–$C_{14}$-aryl, unsubstituted or monosubstituted or polysubstituted by identical or different substituents selected from among
$C_1$–$C_8$-alkyl, substituted or unsubstituted,
$C_3$–$C_{12}$-cycloalkyl,
$C_7$–$C13$-aralkyl,
$C_6$–$C_{14}$-aryl,
halogen,
$C_1$–$C_6$-alkoxy, substituted or unsubstituted,
$C_6$–$C_{14}$-aryloxy,
$SiR^{18}R^{19}R^{20}$ and $O$—$SiR^{18}R^{19}R^{20}$, where $R^{18}$–$R^{20}$ are selected from among hydrogen, $C_1$–$C_8$-alkyl, $C_3$–$C_{12}$-cycloalkyl, $C_7$–$C_{13}$-aralkyl and $C_6$–$C_{14}$-aryl;
five- to six-membered nitrogen-containing heteroaryl radicals, unsubstituted or monosubstituted or polysubstituted by identical or different substituents selected from among
$C_1$–$C_8$-alkyl, substituted or unsubstituted,
$C_3$–$C_{12}$-cycloalkyl,
$C_7$–$C_{13}$-aralkyl,
$C_6$–$C_{14}$-aryl,
halogen,
$C_1$–$C_6$-alkoxy,
$C_6$–$C_{14}$-aryloxy,
$SiR^{18}R^{19}R^{20}$ and $O$—$SiR^{18}R^{19}R^{20}$, where $R^{18}$–$R^{20}$ are selected from among hydrogen, $C_1$–$C_8$-alkyl, $C_3$–$C_{12}$-cycloalkyl, $C_7$–$C_{13}$-aralkyl and $C_6$–$C_{14}$-aryl;

where adjacent radicals $R^1$ to $R^{10}$ together with E may be joined to form a saturated or olefinically unsaturated 5- to 12-membered ring;

$A^1$, $A^3$ are selected from among C—$R^{15}$, C—$R^{16}$, Si—$R^{15}$, Si—$R^{16}$ and N, $A^2$ is selected from among C—$R^{17}$, Si—$R^{17}$ and N, where not more than one $A^j$ is a nitrogen atom and j=1, 2, 3;

$R^{13}$ to $R^{17}$ are selected from among
hydrogen,
$C_1$–$C_8$-alkyl, substituted or unsubstituted,
$C_2$–$C_8$-alkenyl, substituted or unsubstituted, having from one to 4 isolated or conjugated double bonds;
$C_3$–$C_{12}$-cycloalkyl, substituted or unsubstituted,
$C_7$–$C_{13}$-aralkyl,
$C_6$–$C_{14}$-aryl, unsubstituted or monosubstituted or polysubstituted by identical or different substituents selected from among
$C_1$–$C_8$-alkyl, substituted or unsubstituted,
$C_3$–$C_{12}$-cycloalkyl,
$C_7$–$C_{13}$-aralkyl,
$C_6$–$C_{14}$-aryl,
halogen,
$C_1$–$C_6$-alkoxy,
$C_6$–$C_{14}$-aryloxy,
$SiR^{18}R^{19}R^{20}$ and $O$—$SiR^{18}R^{19}R^{20}$, where $R^{18}$–$R^{20}$ are selected from among hydrogen, $C_1$–$C_8$-alkyl, $C_3$–$C_{12}$-cycloalkyl, $C_7$–$C_{13}$-aralkyl and $C_6$–$C_{14}$-aryl;
five- to six-membered nitrogen-containing heteroaryl radicals, unsubstituted or monosubstituted or polysubstituted by identical or different substituents selected from among
$C_1$–$C_8$-alkyl, substituted or unsubstituted,
$C_3$–$C_{12}$-cycloalkyl,
$C_7$–$C_{13}$-aralkyl,
$C_6$–$C_{14}$-aryl,
halogen,
$C_1$–$C_6$-alkoxy,
$C_6$–$C_{14}$-aryloxy,
$SiR^{18}R^{19}R^{20}$ and $O$—$SiR^{18}R^{19}R^{20}$, where $R^{18}$–$R^{20}$ are selected from among $C_1$–$C_8$-alkyl, $C_3$–$C_{12}$-cycloalkyl, $C_7$–$C_{13}$-aralkyl and $C_6$–$C_{14}$-aryl;

where $R^{13}$ to $R^{17}$ together with one or more atoms $A^j$ may form a saturated or unsaturated 5- to 12-membered ring
and $[Y]^-$ is an anion.

These metal compounds can be used for the polymerization and copolymerization of olefins. The present invention also provides a process for the polymerization and copolymerization of olefins using one or more of the metal compounds of the present invention. Furthermore, the present invention provides supported catalysts comprising one or more of the compounds of the present invention for the polymerization or copolymerization of olefins, a process for preparing the supported catalysts of the present invention and a process for the polymerization or copolymerization of olefins using a supported catalyst according to the present invention. Finally, the present invention provides a process for preparing the metal compounds of the present invention.

Polymers and copolymers of olefins are of great economic importance because the monomers are readily available in large quantities and because the polymers can be varied within a wide range by variation of the production process or the processing parameters. In the production process, the catalyst used is of particular significance. Apart from Ziegler-Natta catalysts, various single-site catalysts are of increasing importance. In these single-site catalysts, central atoms which have been examined in detail in recent times are not only Zr as in metallocene catalysts (H.-H. Brintzinger et al., Angew. Chem. 1995, 107, 1255) but also Ni or Pd (WO 96/23010) and Fe and Co (e.g. WO 98/27124). The complexes of Ni, Pd, Fe and Co are also referred to as complexes of late transition metals.

For industrial use, metallocene catalysts have disadvantages. The catalysts are very sensitive to impurities in the industrially available monomers, in the process gas and in the solvents used. Impurities which cause problems are, for example, moisture and oxygen as well as CO, but also Lewis bases in general, e.g. ethers. Furthermore, the price of Zr as central metal in the industrially important zirconocenes is very high.

While Ni or Pd complexes (WO 96/23010) catalyze the formation of highly branched, commercially less interesting polymers, the use of Fe or Co complexes leads to the formation of highly linear polyethylenes.

The abovementioned complexes are polymerization-inactive as such and have to be activated by means of cocatalysts. Cocatalysts used for the polymerization of ethylene are methylaluminoxane ("MAO") or modified methylaluminoxane ("MMAO")in which a certain percentage of the methyl groups have been replaced by isobutyl groups.

However, the use of MAO or other aluminoxanes has disadvantages:

MAO and other aluminoxanes have to be used in a large molar excess; from 100- to 1000-fold excesses are customary. The cocatalyst therefore becomes a significant cost factor for the catalysts.

Aluminoxanes are not molecular defined substances and their ability to activate transition metal complexes depends greatly on the method of preparation and impurities. Furthermore, the storage temperature and the storage time play a role. Quality control is difficult.

Aluminoxanes always have to be stored under refrigeration, because otherwise they tend to form gels. Aluminoxane gels are unsuitable as cocatalysts.

Aluminoxanes have to be used in a large excess and increase the residual ash content of the polymer.

Aluminoxanes are provided commercially as solutions, so that much otherwise worthless solvent has to be transported.

Aluminoxanes, particularly those having $C_1$–$C_4$-alkyl radicals, and their solutions are pyrophoric and require increased safety measures.

Another class of known cocatalysts is made up by strong Lewis acids and salts of noncoordinating or only weakly coordinating anions bearing bulky substituents. Suitable Lewis acids and salts are selected boron compounds bearing electron-withdrawing groups (e.g. trispentafluorophenylborane, N,N-dimethylanilinium tetrakispentafluorophenylborate, tri-n-butylammonium tetrakispentafluorophenylborate, N,N-dimethylanilinium tetrakis(3,5-bisperfluoromethyl)phenylborate, tri-n-butylammonium tetrakis(3,5-bisperfluoromethyl)phenylborate and tritylium tetrakispentafluorophenylborate, usually together with an aluminum alkyl. These activators are described in EP-A 0 468 537 and EP-A 0 426 638. A disadvantage of these catalyst systems is that they are air and moisture sensitive because of the use of aluminum alkyls. Other Lewis bases such as ethers also have to be carefully excluded, likewise CO and $CO_2$.

Also known are palladium complexes of the formula A or B,

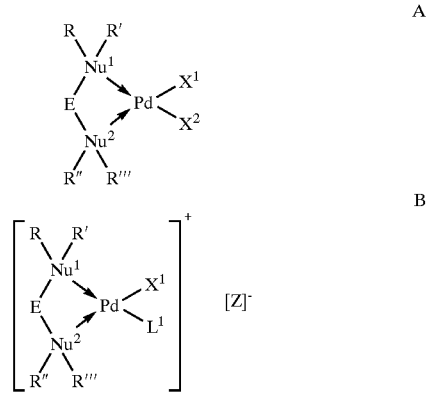

(EP-A 0 827 515) where R, R', R" and R'" are selected from among various alkyl and aryl radicals, E is a bridging element, $Nu^1$ and $Nu^2$ are selected from among N, P and As, and [Z] is a counterion.

If the further ligands $X^1$ and $X^2$ on the Pd are selected from among halogen, aryl, aralkyl and alkyl and $L^1$ is an uncharged ligand such as acetonitrile or diethyl ether, the complexes of the formulae A and B are suitable for preparing polyolefins and olefin copolymers, in particular with polar comonomers. However, the complexes of the formulae A and B have disadvantages in use:

If $X^1$ and $X^2$ are selected from among alkyl, aryl and aralkyl, the complexes are air and moisture sensitive and have a poor storage stability.

If $X^1$ and $X^2$ are each halide, the activity of the complexes is frequently too low for industrial applications.

When Lewis bases, air and moisture have to be carefully excluded, as required by the known catalyst systems, the monomers and suspension media and solvents in the polymerization have to meet particular purity requirements, which generally leads to high costs. Furthermore, the known catalysts have only a limited shelf life.

It is an object of the present invention to find a catalyst system which can be handled without a great outlay in terms of apparatus for exclusion of air and moisture and without purification of monomers, and which requires no activators. A further object is to polymerize and copolymerize olefins using this catalyst system.

We have found that these objects are achieved by the metal compounds defined at the outset.

In formula I,

M is Ni or Pd, preferably Ni;

$Nu^1$ and $Nu^2$ are identical or different and are selected from among N, P and As, preferably identical and selected from among N and P, particularly preferably both P;

the bridging element E is selected from among

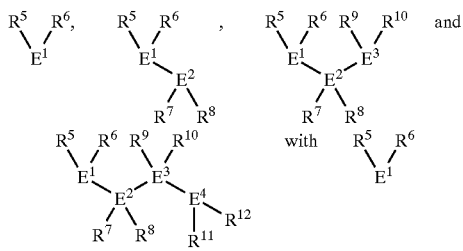

being preferred as bridging element.

$E^1$, $E^2$, $E^3$ and $E^4$ are selected independently from among C, Si and Ge, and are preferably C and Si and particularly preferably C.

$R^1$ to $R^{12}$ are selected independently from among hydrogen, $C_1$–$C_8$-alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and examples of substituted $C_1$–$C_8$-alkyl groups are: monohalogenated and polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_2$–$C_8$-alkenyl having from one to 4 isolated or conjugated double bonds, for example vinyl, 1-allyl, 3-allyl, ω-butenyl, ω-pentenyl, ω-hexenyl, 1-cis-buta-1,3-dienyl or 1-cis-hexa-1,5-dienyl;

examples of substituted $C_2$–$C_8$-alkenyl groups are: isopropenyl, 1-isoprenyl, α-styryl, β-styryl, 1-cis-1,2-phenylethenyl and 1-trans-1,2-phenylethenyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

examples of substituted cycloalkyl groups are: 2-methylcyclopentyl, 3-methylcyclopentyl, cis-2,4-dimethylcyclopentyl, trans-2,4-dimethylcyclopentyl, cis-2,5-dimethylcyclopentyl, trans-2,5-dimethylcyclopentyl, 2,2,5,5-tetramethylcyclopentyl, 2-methylcyclohexyl, 3-methylcyclohexyl, 4-methylcyclohexyl, cis-2,6-dimethylcyclohexyl, trans-2,6-dimethylcyclohexyl, cis-2,6-diisopropylcyclohexyl, trans-2,6-diisopropylcyclohexyl, 2,2,6,6-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,6,6-tetrachlorocyclohexyl, 2-thiomethylcyclopentyl, 2-thiomethylcyclohexyl, 3-thiomethylcyclopentyl, 3-thiomethylcyclohexyl and further derivatives;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

$C_6$–$C_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, substituted by one or more identical or different substituents selected from among $C_1$–$C_8$-alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_8$-alkyl groups are: monohalogenated and polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

halogen, for example fluorine, chlorine, bromine and iodine, particularly preferably fluorine and chlorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy and 9-anthryloxy;

silyl groups $SiR^{18}R^{19}R^{20}$, where $R^{18}$ to $R^{20}$ are selected independently from among hydrogen, $C_1$–$C_8$-alkyl groups, the benzyl group and $C_6$–$C_{14}$-aryl groups; particular preference is given to the trimethylsilyl, triethylsilyl, triisopropylsilyl, diethylisopropylsilyl, dimethylthexylsilyl, tert-butyldimethylsilyl, tert-butyldiphenylsilyl, tribenzylsilyl, triphenylsilyl and tri-para-xylylsilyl groups; particular preference is given to the trimethylsilyl group and the tert-butyldimethylsilyl group;

silyloxy groups $OSiR^{18}R^{19}R^{20}$, where $R^{18}$ to $R^{20}$ are selected independently from among hydrogen, $C_1$–$C_8$-alkyl groups, the benzyl group and $C_6$–$C_{14}$-aryl groups; preference is given to the trimethylsilyloxy, triethylsilyloxy, triisopropylsilyloxy, diethylisopropylsilyloxy, dimethylthexylsilyloxy, tert-butyldimethylsilyloxy, tert-butyldiphenylsilyloxy, tribenzylsilyloxy, triphenylsilyloxy and the tri-para-xylylsilyloxy groups; particular preference is given to the trimethylsilyloxy group and the tert-butyldimethylsilyloxy group;

five- to six-membered nitrogen-containing heteroaryl radicals such as for example N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl;

five- to six-membered nitrogen-containing heteroaryl radicals such as for example N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl, each bearing one or more identical or different substituents selected from among $C_1$–$C_8$-alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

Examples of substituted $C_1$–$C_8$-alkyl groups are: monohalogenated and polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

halogen, for example fluorine, chlorine, bromine and iodine, particularly preferably fluorine and chlorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy and 9-anthryloxy;

silyl groups $SiR^{18}R^{19}R^{20}$, where $R^{18}$ to $R^{20}$ are selected independently from among hydrogen, $C_1$–$C_8$-alkyl groups, the benzyl group and $C_6$–$C_{14}$-aryl groups; particular preference is given to the trimethylsilyl, triethylsilyl, triisopropylsilyl, diethylisopropylsilyl, dimethylthexylsilyl, tert-butyldimethylsilyl, tert-butyldiphenylsilyl, tribenzylsilyl, triphenylsilyl and tri-para-xylylsilyl groups; particular preference is given to the trimethylsilyl group and the tert-butyldimethylsilyl group;

silyloxy groups $OSiR^{18}R^{19}R^{20}$, where $R^{18}$ to $R^{20}$ are selected independently from among hydrogen, $C_1$–$C_8$-alkyl groups, the benzyl group and $C_6$–$C_{14}$-aryl groups; preference is given to the trimethylsilyloxy, triethylsilyloxy, triisopropylsilyloxy, diethylisopropylsilyloxy, dimethylthexylsilyloxy, tert-butyldimethylsilyloxy, tert-butyldiphenylsilyloxy, tribenzylsilyloxy, triphenylsilyloxy and the tri-para-xylylsilyloxy groups; particular preference is given to the trimethylsilyloxy group and the tert-butyldimethylsilyloxy group.

In a preferred embodiment, $R^1$ and $R^2$ and also $R^3$ and $R^4$ are identical in pairs and are selected from among tert-butyl and cyclohexyl radicals. In a particularly preferred embodiment, $R^5$ and $R^6$ are identical and are very particularly preferably hydrogen.

In a particular embodiment, $R^1$ and a suitable $R^2$ to $R^{12}$ together with one or more $E^i$, where i=1, 2, 3 or 4, may form a saturated or unsaturated 5- to 12-membered ring. In a further particular embodiment, $R^3$ and a suitable $R^5$ to $R^{12}$ together with one or more $E^i$, where i=1, 2, 3 or 4, may form a saturated or unsaturated 5- to 12-membered ring. For example, $R^1$ and $R^5$ may together be:

—$(CH_2)_3$-(trimethylene), —$(CH_2)_4$-(tetramethylene), —$(CH_2)_5$-(pentamethylene), —$(CH_2)_6$-(hexamethylene), —$CH_2$—CH=CH—, —$CH_2$—CH=CH—$CH_2$—, —CH=CH—CH=CH—, —O—$CH_2$—O—, —O—CHMe—O—, —O—CH($C_6H_5$)—O—, —O—$CH_2$—$CH_2$—O—, —O—$CMe_2$—O—, —NMe—$CH_2$—$CH_2$—NMe—, —NMe—$CH_2$—NMe— or —O—$SiMe_2$—O— where Me=$CH_3$.

$A^1$ and $A^3$ are selected from among C—$R^{15}$, C—$R^{16}$, Si—$R^{15}$, Si—$R^{16}$ and N, where $A^1$ and $A^3$ may be identical but do not have to be.

$A^2$ is selected from among C—$R^{17}$, Si—$R^{17}$ and N. Here, not more than one $A^j$, where j=1, 2, 3, is a nitrogen atom.

$R^{13}$ to $R^{17}$ are identical or different and are selected from among hydrogen, C$_1$–C$_8$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably C$_1$–C$_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably C$_1$–C$_4$-alkyl such as methyl, ethyl, n-propyl, isopropyl, n-butyl, isobutyl, sec-butyl and tert-butyl;

examples of substituted C$_1$–C$_8$-alkyl groups are: monohalogenated and polyhalogenated C$_1$–C$_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

C$_2$–C$_8$-alkenyl having one to 4 isolated or conjugated double bonds, for example vinyl, 1-allyl, 3-allyl, ω-butenyl, ω-pentenyl, ω-hexenyl, 1-cis-buta-1,3-dienyl or 1-cis-hexa-1,5-dienyl.

examples of substituted C$_2$–C$_8$-alkenyl groups are: isopropenyl, 1-isoprenyl, α-styryl, β-styryl, 1-cis-1,2-phenylethenyl or 1-trans-1,2-phenylethenyl.

C$_3$–C$_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

examples of substituted cycloalkyl groups are: 2-methylcyclopentyl, 3-methylcyclopentyl, cis-2,4-dimethylcyclopentyl, trans-2,4-dimethylcyclopentyl, cis-2,5-dimethylcyclopentyl, trans-2,5-dimethylcyclopentyl, 2,2,5,5-tetramethylcyclopentyl, 2-methylcyclohexyl, 3-methylcyclohexyl, 4-methylcyclohexyl, cis-2,6-dimethylcyclohexyl, trans-2,6-dimethylcyclohexyl, cis-2,6-diisopropylcyclohexyl, trans-2,6-diisopropylcyclohexyl, 2,2,6,6-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,6,6-tetrachlorocyclohexyl, 2-thiomethylcyclopentyl, 2-thiomethylcyclohexyl, 3-thiomethylcyclopentyl, 3-thiomethylcyclohexyl and further derivatives;

NO$_2$, halogen selected from among fluorine, chlorine, bromine and iodine, particularly preferably fluorine and chlorine, C$_7$–C$_{13}$-aralkyl, preferably C$_7$–C$_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

C$_6$–C$_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

C$_6$–C$_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, substituted by one or more identical or different substituents selected from among C$_1$–C$_8$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably C$_1$–C$_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably C$_1$–C$_4$-alkyl such as methyl, ethyl, n-propyl, isopropyl, n-butyl, isobutyl, sec-butyl and tert-butyl;

examples of substituted C$_1$–C$_8$-alkyl groups are: monohalogenated and polyhalogenated C$_1$–C$_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

C$_3$–C$_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

C$_7$–C$_{13}$-aralkyl, preferably C$_7$–C$_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

C$_6$–C$_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

halogen, for example fluorine, chlorine, bromine and iodine, particularly preferably fluorine and chlorine;

C$_1$–C$_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

C$_6$–C$_{14}$-aryloxy groups such as phenoxy, ortho-cresyloxy, meta-cresyloxy, para-cresyloxy, α-naphthoxy, β-naphthoxy and 9-anthryloxy;

silyl groups SiR$^{18}$R$^{19}$R$^{20}$, where R$^{18}$ to R$^{20}$ are selected independently from among hydrogen, C$_1$–C$_8$-alkyl groups, the benzyl groups and C$_6$–C$_{14}$-aryl groups; preferably the trimethylsilyl, triethylsilyl, triisopropylsilyl, diethylisopropylsilyl, dimethylthexylsilyl, tert-butyldimethylsilyl, tert-butyldiphenylsilyl, tribenzylsilyl, triphenylsilyl and tri-para-xylylsilyl groups; particularly preferably the trimethylsilyl group and the tert-butyldimethylsilyl group;

silyloxy groups OSiR$^{18}$R$^{19}$R$^{20}$, where R$^{18}$ to R$^{20}$ are selected independently from among hydrogen, C$_1$–C$_8$-alkyl groups, the benzyl groups and C$_6$–C$_{14}$-aryl groups; preferably the trimethylsilyloxy, triethylsilyloxy, triisopropylsilyloxy, diethylisopropylsilyloxy, dimethylthexylsilyloxy, tert-butyldimethylsilyloxy, tert-butyldiphenylsilyloxy, tribenzylsilyloxy, triphenylsilyloxy and the tri-para-xylylsilyloxy groups; particularly preferably the trimethylsilyloxy group and the tert-butyldimethylsilyloxy group;

five- to six-membered nitrogen-containing heteroaryl radicals such as for example N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl;

five- to six-membered nitrogen-containing heteroaryl radicals such as for example N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl, each bearing one or more identical or different substituents selected from among $C_1$–$C_8$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_8$-alkyl groups are: mono-halogenated and polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

halogen, for example fluorine, chlorine, bromine and iodine, particularly preferably fluorine and chlorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy and 9-anthryloxy;

silyl groups $SiR^{18}R^{19}R^{20}$, where $R^{18}$ to $R^{20}$ are selected independently from among hydrogen, $C_1$–$C_8$-alkyl groups, the benzyl groups and $C_6$–$C_{14}$-aryl groups; preferably the trimethylsilyl, triethylsilyl, triisopropylsilyl, diethylisopropylsilyl, dimethylthexylsilyl, tert-butyldimethylsilyl, tert-butyldiphenylsilyl, tribenzylsilyl, triphenylsilyl and tri-para-xylylsilyl groups; particularly preferably the trimethylsilyl group and the tert-butyldimethylsilyl group;

silyloxy groups $OSiR^{18}R^{19}R^{20}$, where $R^{18}$ to $R^{20}$ are selected independently from among hydrogen, $C_1$–$C_8$-alkyl groups, benzyl radicals and $C_6$–$C_{14}$-aryl groups; preferably the trimethylsilyloxy, triethylsilyloxy, triisopropylsilyloxy, diethylisopropylsilyloxy, dimethylthexylsilyloxy, tert-butyldimethylsilyloxy, tert-butyldiphenylsilyloxy, tribenzylsilyloxy, triphenylsilyloxy and tri-para-xylylsilyloxy groups; particularly preferably the trimethylsilyloxy group and the tert-butyldimethylsilyloxy group.

Here, two radicals $R^{13}$ to $R^{17}$ with or without one or more groups $A^j$ may form a saturated or unsaturated 5- to 12-membered ring which may in turn bear substituents. Thus, for example $R^{15}$ and $R^{17}$ may together be:

—$(CH_2)_3$-(trimethylene), —$(CH_2)_4$-(tetramethylene), —$(CH_2)_5$-(pentamethylene), —$(CH_2)_6$-(hexamethylene), —$CH_2$—CH═CH—, —$CH_2$—CH═CH—$CH_2$—, —CH═CH—CH═CH—, —O—$CH_2$—O—, —O—CHMe—O—, —O—CH—$(C_6H_5)$—O—, —O—$CH_2$—$CH_2$—O—, —O—$CMe_2$—O—, —NMe—$CH_2$—$CH_2$—NMe—, —NMe—$CH_2$—NMe— or —O—$SiMe_2$—O— where Me═$CH_3$.

In a very particularly preferred embodiment, $A^1$ and $A^3$ are each C—$R^{15}$, $R^{13}$ and $R^{15}$ are hydrogen, $A^2$ is C—$R^{17}$, and $R^{14}$ and $R^{17}$ together form a 1,3-butadiene-1,4-diyl unit which may in turn be substituted by radicals $Z^1$ to $Z^5$ (formula IV).

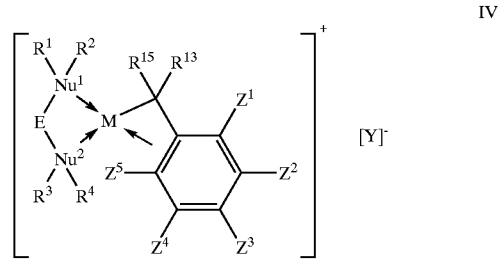

IV

In formula IV, $Z^1$ to $Z^5$ are identical or different and are selected from among hydrogen, $C_1$–$C_8$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_8$-alkyl groups are: monohalogenated and polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_2$–$C_8$-alkenyl having one to 4 isolated or conjugated double bonds, for example vinyl, 1-allyl, 3-allyl, ω-butenyl, ω-pentenyl, ω-hexenyl, 1-cis-buta-1,3-dienyl or 1-cis-hexa-1,5-dienyl;

examples of substituted $C_2$–$C_8$-alkenyl groups are: isopropenyl, 1-isoprenyl, α-styryl, β-styryl, 1-cis-1,2-phenylethenyl or 1-trans-1,2-phenylethenyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

examples of substituted cycloalkyl groups are: 2-methylcyclopentyl, 3-methylcyclopentyl, cis-2,4-dimethylcyclopentyl, trans-2,4-dimethylcyclopentyl, cis-2,5-dimethylcyclopentyl, trans-2,5-dimethylcyclopentyl, 2,2,5,5-tetramethylcyclopentyl, 2-methylcyclohexyl, 3-methylcyclohexyl, 4-methylcyclohexyl, cis-2,6-dimethylcyclohexyl, trans-2,6-dimethylcyclohexyl, cis-2,6-diisopropylcyclohexyl, trans-2,6-diisopropylcyclohexyl, 2,2,6,6-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,6,6-tetrachlorocyclohexyl, 2-thiomethylcyclopentyl, 2-thiomethylcyclohexyl, 3-thiomethylcyclopentyl, 3-thiomethylcyclohexyl and further derivatives;

$NO_2$, halogen selected from among fluorine, chlorine, bromine and iodine, preferably fluorine and chlorine, $C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl.

Here, two adjacent radicals $Z^1$ to $Z^5$ together with the phenyl system may form a 5- to 12-membered ring. Thus, for example, $Z^1$ and $Z^2$ or $Z^2$ and $Z^3$ may together be:

—$(CH_2)_3$-(trimethylene), —$(CH_2)_4$-(tetramethylene), —$(CH_2)_5$-(pentamethylene), —$(CH_2)_6$-(hexamethylene), —$CH_2$—CH=CH—, —$CH_2$—CH=CH—$CH_2$—, —CH=CH—CH=CH—, —O—$CH_2$—O—, —O—CHMe—O—, —O—CH—$(C_6H_5)$—O—, —O—$CH_2$—$CH_2$—O—, —O—$CMe_2$—O—, —NMe—$CH_2$—$CH_2$—NMe—, —NMe—$CH_2$—NMe— or —O—$SiMe_2$—O— where Me=$CH_3$.

Anions [Y]⁻ which have been found to be useful are weakly coordinating anions as are used in the coordination chemistry of nickel and palladium.

A preferred class of anions is made up by those of the formula $[BAr_4]^-$.

Here, Ar are $C_6$–$C_{14}$-aromatic radicals which may be identical or different and may be substituted by one or more substituents selected from among halogen, for example fluorine, chlorine, bromine and iodine, preferably fluorine and chlorine and particularly preferably fluorine;

$C_1$–$C_8$-alkyl such as for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_8$-alkyl groups are: monohalogenated and polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl; also —$CH_2CN$;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

examples of substituted $C_6$–$C_{14}$-aryl groups are: pentafluorophenyl, 2,4,6-trichlorophenyl and 3,5-dicyanophenyl.

Particularly preferred anions [Y]⁻ are, for example, tetraphenylborate, tetrakisperfluorophenylborate $[B(C_6F_5)_4]^-$ and tetrakis(3,5-bistrifluoromethylphenyl)borate $[B(C_6H_3\{CF_3\}_2)_4]^-$.

Further particularly useful anions are $BF_4^-$, $PF_6^-$, $AsF_6^-$, $SbF_6^-$, $ClO_4^-$, $CF_3SO_3^-$ or $CF_3CO_2^-$.

A particular advantage of these particularly useful anions is that they can be used in the form of their acids, while numerous borates are commercially available only as expensive N,N-dimethylanilinium salts.

The process for preparing the metal compound of the present invention advantageously comprises reacting a metal complex of the formula II

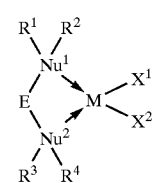

II with two equivalents of a compound of the formula III a or at least one equivalent of a compound of the formula III b

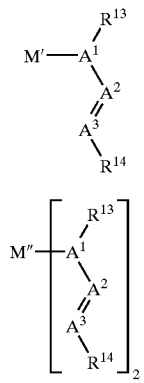

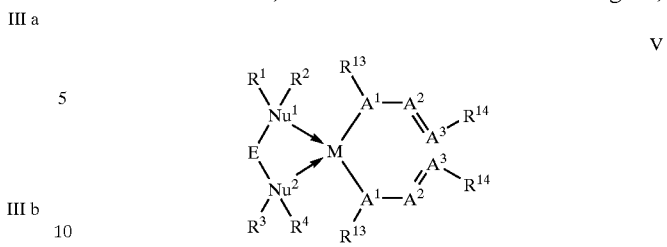

and subsequently adding one equivalent of an acid to eliminate one equivalent of the anion of the compound III.

In formula II, $X^1$ and $X^2$ are identical or different and are selected from among the halogens, for example fluorine, chlorine, bromine and iodine, preferably chlorine and bromine.

In compounds of the formula III a, M' is selected from among Li, Na, K, Rb, Cs and $MgX^3$, where $X^3$ is selected from among chlorine, bromine and iodine. In preferred embodiments, M' is Li or MgBr or MgCl.

In the compounds of the formula III b, M" is selected from among Mg and Ca, with preference being given to Mg.

The preparation of the metal complexes of the formula II is described in EP 0 827 515. Numerous compounds of the formula III a or III b are commercially available or can be prepared by standard methods as described, for example, in Houben-Weyl, Methoden der organischen Chemie, Thieme Verlag Stuttgart, Volumes 13/1 and 13/2a, 1970.

The reaction conditions for the reaction of the metal complexes of the formula II with the compound of the formula III a or III b are not critical per se and can be chosen within wide limits. The order of addition of the reagents is not critical. Suitable reaction temperatures are from −78° C. to +125° C., preferably from −40° C. to room temperature. The reaction can be carried out under atmospheric pressure or under slightly subatmospheric or superatmospheric pressure, with pressures of from 10 mbar to 10 bar being useful. The reaction is preferably carried out at atmospheric pressure.

The compounds of the formulae III a and III b are generally air and moisture sensitive, so that it is appropriate to work in the absence of air and moisture.

It has been found to be useful to carry out the reaction in a diluent. Diluents can be selected from among:

paraffins such as n-pentane, n-hexane, n-heptane, isooctane, cyclohexane and isododecane, aromatics such as benzene, toluene, ethylbenzene, o-xylene, m-xylene, p-xylene and mixtures of various aromatics;

noncyclic or cyclic ethers such as diethyl ether, diisopropyl ether, di-n-butyl ether, methyl tert-butyl ether, 1,2-dimethoxyethane, diglycol dimethyl ether, tetrahydrofuran, 1,4-dioxane;

sulfolane and HMPA (hexamethylphosphoramide), and mixtures of the abovementioned diluents. Preferred diluents are n-pentane, n-hexane and diethyl ether.

The diluent can act as solvent or suspension medium.

The intermediate, to which the formula V can be assigned, can be isolated and purified, for which purpose the operations known from coordination chemistry, for example extraction, evaporation, precipitation and reprecipitation, crystallization or chromatography, are suitable. This step can be useful, for example, for removing traces of starting material II or metal salts of the formula $M'X^1$, $M'X^2$, $M''(X^1)_2$ or $M''X^1X^2$, as are formed depending on whether III a or III b is used.

However, the purification step can also be omitted and IV can be processed further in situ.

According to the present invention, the intermediate IV is then reacted with a derivative of the anion $[Y]^-$. Suitable derivatives are the conjugated Brønsted acids HY, also ammonium salts such as $[H_xNR^*_{4-x}]$, where x is an integer from 1 to 4 and the radicals R* are identical or different and are selected from among $C_1$–$C_8$-alkyl and $C_6$–$C_{14}$-aryl, with $C_1$–$C_8$-alkyl and $C_6$–$C_{14}$-aryl being as defined for $R^1$. Further suitable derivatives are the salts of $Y^-$ with oxonium ions. A particularly preferred oxonium ion is $[H(OEt_2)_2]^+$ where $Et=C_2H_5$.

Preference is given to reacting the intermediate IV with a Brønsted acid of $[Y]^-$. These acids of the particularly useful ions $BF_4^-$, $PF_6^-$, $AsF_6^-$, $SbF_6^-$, $ClO_4^-$, $CF_3SO_3^-$ or $CF_3CO_2-$ can be purchased at low cost.

The reaction conditions are generally not critical. The order of addition of the reactants plays no significant role either with regard to purity or with regard to the yield. Suitable reaction temperatures are from −95° C. to +125° C., preferably from −40° C. to room temperature. The reaction can be carried out under atmospheric pressure, but also under slightly subatmospheric or superatmospheric pressure, with pressures of from 10 mbar to 10 bar being useful. The reaction is preferably carried out at atmospheric pressure.

The novel, generally ionic metal compounds of the formula I can be isolated from the reaction mixtures by operations with which those skilled in the art are familiar, for example extraction, evaporation, precipitation and reprecipitation or crystallization, and can be purified further if necessary. They are generally obtained in good purity and can be used immediately for polymerization. However, owing to their insensitivity to air and moisture, they can also be stored for weeks without special precautions and can then be used without a drop in activity.

The complexes of the present invention can be used directly without further activators for the polymerization or copolymerization of olefins. It is possible to use one or more different metal compounds according to the present invention simultaneously.

Pressure and temperature conditions during the polymerization can be chosen within wide limits. As regards the pressure, a range from 0.5 bar to 4000 bar has been found to be suitable; preference is given to from 10 to 75 bar or high-pressure conditions of from 500 to 2500 bar. As regards temperature, a range from from 0 to 120° C. has been found to be suitable; preference is given to from 40 to 100° C., particularly preferably from 50 to 85° C.

As monomers, mention may be made of the following olefins: ethylene, propylene, 1-butene, 1-pentene, 1-hexene, 1-octene, 1-decene or 1-undecene, with particular preference being given to ethylene.

The suitable comonomers include α-olefins, for example from 0.1 to 20 mol % of 1-butene, 1-pentene, 1-hexene, 4-methyl-1-pentene, 1-octene, 1-decene or 1-undecene. Further suitable comonomers are isobutene and styrene, also internal olefins such as cyclopentene, cyclohexen, norbornene and norbornadiene.

Solvents which have been found to be useful are toluene, ortho-xylene, meta-xylene, para-xylene and ethylbenzene and mixtures of these, also diethyl ether, tetrahydrofuran, chlorobenzene, 1,3-dichlorobenzene, dichloromethane and, under high-pressure conditions, supercritical ethylene.

The polymerization catalyzed by the metal compounds of the present invention can be regulated by means of hydrogen, i.e. the molecular weight of the polymers obtainable by means of the catalyst system of the present invention can be lowered by addition of hydrogen. If sufficient hydrogen is added, waxes are obtained; the hydrogen concentration required also depends on the type of polymerization plant used.

For the metal compounds of the present invention to be able to be used in modern polymerization processes such as suspension processes, bulk polymerization processes or gas-phase processes, it is necessary for them to be immobilized on a solid support. Otherwise, polymer morphology problems (lumps, deposits on walls, blockages in lines or heat exchangers) can result and force shutdown of the plant. Such an immobilized metal compound is referred to as a catalyst.

It has been found that the metal compounds of the present invention can be readily deposited on a solid support. Suitable support materials are, for example, porous metal oxides of metals of groups 2 to 14 or mixtures of these, also sheet silicates and zeolites. Preferred examples of metal oxides of groups 2 to 14 are $SiO_2$, $B_2O_3$, $Al_2O_3$, MgO, CaO and ZnO. Preferred sheet silicates are montmorillonites or bentonites; as zeolite, preference is given to using MCM-41.

Particularly preferred support materials are spherical silica gels and aluminosilicate gels of the formula $SiO_2 \cdot a \, Al_2O_3$, where a is generally in the range from 0 to 2, preferably from 0 to 0.5. Such silica gels are commercially available, e.g. Silica Gel SG 332, Sylopol® 948 or 952 or S 2101 from W. R. Grace or ES 70X from Crosfield.

As particle size of the support material, mean particle diameters of from 1 to 300 μm have been found to be useful; preference is given to from 20 to 80 μm. These particle diameters are determined by known methods such as sieve methods. The pore volume of these supports is from 1.0 to 3.0 ml/g, preferably from 1.6 to 2.2 ml/g and particularly preferably from 1.7 to 1.9 ml/g. The BET surface area is from 200 to 750 m$^2$/g, preferably from 250 to 400 m$^2$/g.

To free the support material of adhering impurities, in particular moisture, the support materials can be baked prior to doping, with temperatures of from 45 to 1000° C. being suitable. Temperatures of from 100 to 750° C. are particularly useful for silica gels and other metal oxides. This baking can be carried out for a period of from 0.5 to 24 hours, preferably from 1 to 12 hours. The pressure conditions depend on the method chosen; baking can be carried out in a fixed-bed process, in a stirred vessel or else in a fluidized-bed process. Baking can quite generally be carried out at atmospheric pressure. However, reduced pressures of from 0.1 to 500 mbar are advantageous; a range from 1 to 100 mbar is particularly advantageous and a range from 2 to 20 mbar is very particularly advantageous. On the other hand, it is advisable to carry out a fluidized-bed process under slightly superatmospheric pressure in the range from 1.01 bar to 5 bar, preferably from 1.1 to 1.5 bar.

Chemical pretreatment of the support material with an alkyl compound such as an aluminum alkyl, a lithium alkyl or an aluminoxane is likewise possible.

However, owing to the low sensitivity of the metal compounds of the present invention toward Lewis bases, baking and chemical pretreatment of the support material can be omitted.

A polymerization by the suspension method is carried out using suspension media in which the desired polymer is insoluble or only slightly soluble, because otherwise deposits of product occur in the parts of the plant in which the product is separated from the suspension medium and force repeated shutdowns and cleaning operations. Suitable suspension media are saturated hydrocarbons such as propane, n-butane, isobutane, n-pentane, isopentane, n-hexane, isohexane and cyclohexane, with preference being given to isobutane.

Pressure and temperature conditions during the polymerization can be chosen within wide limits. As regards pressure, a range from 0.5 bar to 150 bar has been found to be useful; preference is given to from 10 to 75 bar. As regards temperature, a range from 0 to 120° C. has been found to be useful; preference is given to from 40 to 100° C.

As monomers, mention may be made of the following olefins: ethylene, propylene, 1-butene, 1-pentene, 1-hexene, 1-octene, 1-decene and 1-undecene.

Suitable comonomers include α-olefins, for example from 0.1 to 20 mol % of 1-butene, 1-pentene, 1-hexene, 4-methyl-1-pentene, 1-octene, 1-decene and 1-undecene. Further suitable comonomers are isobutene and styrene, also internal olefins such as cyclopentene, cyclohexene, norbornene and norbornadiene.

Furthermore, the catalysts of the present invention have been found to be hydrogen-regulatable, i.e. the molecular weight of the polymers obtainable by means of the catalysts of the present invention can be lowered by addition of hydrogen. If sufficient hydrogen is added, waxes are obtained; the hydrogen concentration required also depends on the type of polymerization plant used. Addition of hydrogen increases the activity of the catalysts of the present invention.

The catalysts of the present invention can also be used together with one or more other polymerization catalysts known per se. Thus, they can be used together with Ziegler-Natta catalysts, supported metallocene catalysts of transition metals of groups IV to VI of the Periodic Table of the Elements, catalysts comprising late transition metals (WO 96/23010), Fe or Co complexes containing pyridyldiimine ligands, as are disclosed in WO 98/27124, or chromium oxide catalysts of the Phillips type.

It is possible to mix various catalysts with one another and to introduce them into the polymerization vessel together or to use cosupported complexes on a common support or else to introduce different catalysts separately into the polymerization vessel at the same point or at different points.

The invention is illustrated below by means of working examples.

General remarks: the syntheses and purification operations were, unless indicated otherwise, carried out under strict exclusion of air and moisture. All solvents were dried by standard methods immediately before use (as described, for example, in Organikum, 3rd reprint of the 15th edition, VEB Deutscher Verlag der Wissenschaften, Leipzig 1984). The melting points are not corrected. The $^1$H-NMR spectra were measured using tetramethylsilane as internal standard.

The starting materials and reagents listed below were prepared by literature methods or purchased:

($\eta^2$-trans-stilbene)[{(bis(di-t-butylphosphino)]methane-$\kappa^2$P} nickel(0)] as described in EP-A 0 827 515 or by a method analogous to that described by P. Hofmann et al., Z. Naturforsch. 1990, 45b, 897 and DE-A 40 34 604;

bis(dicyclohexylphosphino)methane: F. I. Joslin et al., Polyhedron 1991, 10, 1713 and J. S. Yu, I. P. Rothwell, J. Chem. Soc., Chem. Commun., 1992, 632.

The following abbreviations are employed: Me=$CH_3$; Et=$C_2H_5$, Ph=$C_6H_5$; PE=polyethylene.

1M PhCH$_2$MgCl (benzylmagnesium chloride) in diethyl ether was purchased from Aldrich;

[H(OEt$_2$)$_2$] [B(C$_6$H$_3${CF$_3$}$_2$)$_4$] was synthesized by the literature method of M. Brookhart et al., Organometallics 1992, 11, 3920.

1. SYNTHESIS EXAMPLES

Synthesis Example 1.1

Synthesis of [$\eta_3$-(1-benzyl)benzyl][bis(di-t-butylphosphino)methane-$\kappa^2$P] nickel(II)-tetrakis[3,5-bis(trifluoromethyl)phenyl]borate, [(dtbpm-$\kappa^2$P,P')Ni($\eta^3$—CH(CH$_2$Ph)Ph]$^+$[B(C$_6$H$_3${CF$_3$}$_2$)$_4$]$^-$ (formula 1)

In a Schlenk tube, 200 mg (0.37 mmol) of ($\eta^2$-trans-stilbene)-[{bis(di-t-butylphosphino)]methane-$\kappa^2$P}nickel (0)] and 372.5 mg (0.37 mmol) of the acid [H(OEt$_2$)$_2$][B(C$_6$H$_3${CF$_3$}$_2$)$_4$] were dissolved at 0° C. in 20 ml of diethyl ether and stirred for 25 min. The solution was admixed with 20 ml of pentane, resulting in precipitation of a light-brown solid. The supernatant solution was decanted off and the solid was washed with 5 ml of pentane and dried in a high vacuum.

Yield: 476 mg (0.34 mmol, 91% of theory)

Elemental analysis for C$_{43}$H$_{63}$P$_2$NiBF$_{24}$:

calculated: C, 53.76; H, 4.51; P, 4.40.

found: C, 53.67; H, 4.60; P, 4.31.

Melting point: 158° C. (decomposition)

$^1$H-NMR (500 MHz, d$_6$-acetone, T=298 K): δ=1.26 (d, $^3J_{PH}$=13.8 Hz, 9 H, C(C$\underline{H}_3$)$_3$), 1.43 (d, $^3J_{PH}$=13.8 Hz, 9 H, C(C$\underline{H}_3$)$_3$), 1.61 (d, $^3J_{PH}$=14.2 Hz, 9 H, C(C$\underline{H}_3$)$_3$), 1.63 (d, $^3J_{PH}$=14.2 Hz, 9H, C(C$\underline{H}_3$)$_3$), 3.13 (m, 2H, C$\underline{H}_2$Ph), 3.27 (m, 2H, PC$\underline{H}_2$P), 3.83 (m, 1H, NiC$\underline{H}$CH$_2$), 6.86 (d, 1H, Ar$_1$-o-H), 7.13 (m, N=44.9 Hz, 6 H, Ph—$\underline{H}$ and Ar$_1$-o-$\underline{H}$), 7.52 (t, $^3J_{HH}$=7.5 Hz, 1 H, Ar$_1$-m-H), 7.52 (s, p-H, 4H, [B(C$_6$H$_3${CF$_3$}$_2$)$_4$], 7.58 (t, $^3J_{HH}$=7.5 Hz, 1 H, Ar$_1$-m-H), 7.74 (m, 1 H, Ar$_1$-p-H), 7.79 (s, 8 H, o-H [B(C$_6$H$_3${CF$_3$}$_2$)$_4$])

$^{31}$P-NMR (122 MHz, d$_8$-THF): δ=16.8 [d (2J=20.86 Hz)], 29.6 [d (2J=20.86 Hz)]

IR (KBr): ν[cm-1]=2966 (w), 1611 (w), 1473 (w), 1355 (m), 1279 (s) 1163 (m), 1128 (s), 885 (w), 839 (w), 744 (w), 716 (w), 682 (w), 669 (w)

MS (LT-FAB): m/e=543.4 [K]$^+$ with correct isotope pattern

Synthesis Example 1.2

Synthesis of ($\eta^3$-benzyl) [bis(di-t-butylphosphino)methane-$\kappa^2$P]nickel(II)-tetrakis[3,5-bis(trifluoromethyl)phenyl]borate, [(dtbpm-$\kappa^2$P)Ni($\eta^3$—CH$_2$Ph]+[B(C$_6$H$_3${CF$_3$}$_2$)$_4$]$^-$ (formula 2)

60 mg (138.6 μmol) of (dtbpm-$\kappa^2$P)NiCl$_2$ were suspended in 15 ml of pentane and cooled to -40° C. 0.28 ml (280 μmol) of PhCH$_2$MgCl (1M in diethyl ether) was added and the mixture was stirred at -40° C. for 4 hours. The pentane solution became pale red. The solution was siphoned off and the solid was washed twice with pentane. The product was subsequently obtained from the residue by multiple extraction at -50° C. using diethyl ether. The ether solution was filtered through Celite® and allowed to drip directly on to 100 mg (99 μmol) of [H(OEt$_2$)$_2$][B(C$_6$H$_3${CF$_3$}$_2$)$_4$]. This gave an orange solution which slowly became darker during the dropwise addition. The precipitate was extracted cold a number of times using 3 ml each time of diethyl ether, and the combined organge extracts were siphoned from the precipitated solid and concentrated by evaporation under reduced pressure. The product was precipitated by addition of pentane. The product was purified by dissolution in ether and precipitation with pentane, which was repeated a second time.

Yield: 46 mg (25%)

Elemental analysis for C$_{56}$H$_{57}$F$_{24}$P$_2$NiB:

calculated: C, 51.05; H, 4.36; P, 4.70.

found: C, 50.98; H, 4.19; P, 4.73.

Melting point: 195° C.

$^1$H-NMR (300 MHz, d$_6$-acetone, T=298 K): δ=1.33 (d, $^3J_{PH}$=13.9 Hz, 18H, C(C$\underline{H}_3$)$_3$), 1.58 (d, $^3J_{PH}$=14.5 Hz, 18H, C(C$\underline{H}_3$)$_3$), 2.60 (dd, $^2J_{PH}$=6.0 Hz, 2J$_{PH}$=3.2 Hz, 2H, P—C$\underline{H}_2$—P), 3.39 (dd, $^3J_{PH}$=9.21 Hz, $^3J_{PH}$=1.5 Hz, 2H, C$\underline{H}_2$—Ph), 6.77 (d, $^3J_{HH}$=6.8 Hz, 2H, o-benzyl-H), 7.52 (t, $^3J_{HH}$=7.35, 1H, p-benzyl-H), 7.66 (s, 4H, p-H of the [B(C$_6$H$_3${CF$_3$}$_2$)$_4$]), 7.77 (m, 10H, o-H of [B(C$_6$H$_3${CF$_3$}$_2$)$_4$]+m-benzyl-H)

$^{31}$P-NMR (122 MHz, C$_6$D$_6$, T=298 K): δ=20.0 (d, 2J$_{PP}$=13.0 Hz), 36.0 (d, 2J$_{PP}$=13.0 Hz)

$^{13}$C-NMR (126 MHz, d$_6$-acetone, T=298 K): δ=26.61 (t, $^1J_{PC}$=13.7 Hz, P—$\underline{C}$H$_2$—P), 31.11 (d, $^2J_{PC}$=2.4 Hz, C($\underline{C}$H$_3$)$_3$), 31.19 (d, $^2J_{PC}$=7.6 Hz, C($\underline{C}$H$_3$)$_3$), 37.02 (d, $^1J_{PC}$=5.2 Hz, $\underline{C}$(CH$_3$)$_3$), 37.49 (dd, $^1J_{PC}$=10.4 Hz, 3J$_{PC}$=4.7 Hz, $\underline{C}$(CH$_3$)$_3$), 54.88 (m, N=75.5 Hz, $\underline{C}$H$_2$-Ph), 114.17 (d, $^3J_{PC}$=4.7 Hz, o-C benzyl), 118.48 (s, p-C [B(C$_6$H$_3${CF$_3$}$_2$)$_4$]), 125.42 (q, $^1J_{CF}$=271.82 Hz, $\underline{C}$F$_3$), 128.66 (p-C benzyl), 129.98 (qm, $^2J_{CF}$=31 Hz, m-C [B(C$_6$H$_3${CF$_3$}$_2$)$_4$]), 135.58 (s, o-C [B(C$_6$H$_3${CF$_3$}$_2$)$_4$]), 136.64 (d, J=1.9 Hz, m-C benzyl), 162.64 (q, $^1J_{CB}$=49.9 Hz, i-C [B(C$_6$H$_3${CF$_3$}$_2$)$_4$])

IR (KBr): ν[cm$^{-1}$]=2966 w, 1611 w, 1476 w, 1355 m, 1277 s, 1168 m, 1131 s, 888 w, 839 w, 807 w, 757 w, 745 w, 716 w, 682 m, 670 m.

MS (LT-FAB$^+$): m/e=453.2 [K$^+$] with correct isotope pattern

Synthesis Example 1.3

Synthesis of ($\eta^3$-benzyl) [bis (dicyclohexylphosphino)methane-$\kappa^2$P] nickel (II)-tetrakis[3,5-bis(trifluoromethyl)phenyl]borate, [(dcpm-$\kappa^2$P)Ni($\eta^3$-CH$_2$Ph]$^+$[B(C$_6$H$_3${CF$_3$}$_2$)$_4$]$^-$ 1.3.1. Synthesis of dichloro[bis(dicyclohexylphosphino)methane-$\kappa^2$P]nickel (II), (dcpm-$\kappa^2$P) NiCl$_2$ 1.3 g (6.90 mmol) of NiCl$_2$ were admixed with 50 ml of ethanol. The suspension was heated to just below boiling, and the NiCl$_2$ went into solution. 3.0 g (7.34 mmol) of bis(dicyclohexylphosphino)-methane (dcpm) were then added and the mixture was again heated until it started to boil. The solution became deep red. It was refluxed for another 2 hours and then slowly cooled, resulting in crystallization of the product. The mother liquor was siphoned off and evaporated under reduced pressure; the precipitated crystals were combined with the others and dried.

Yield: 2.9 g (70%)

Elemental analysis for $C_{25}H_{46}P_2NiCl_2$:

calculated: C, 55.79; H, 8.62; Cl, 13.18; P, 11.51.

found: C, 55.62; H, 8.74; Cl, 13.19; P, 11.54.

Melting point: 347° C. (decomposition)

$^1$H-NMR (300 MHz, $CDCl_3$, T=298 K): δ=1.2-2.6 (6 m, Cy-H, P—C$\underline{H}_2$—P, 46)

$^{31}$P-NMR (122 MHz, $CDCl_3$, T=298 K): δ=−24.06 (s)

$^{13}$C-NMR (75 MHz, $CDCl_3$, T=298 K): δ=13.6 (t, $^1J_{PC}$=20.3 Hz, P—$\underline{C}H_2$—P), 25.7 (s, Cy-$\underline{C}$), 26.6 (s, Cy-$\underline{C}$), 27.0 (s, Cy-$\underline{C}$), 27.8 (s, Cy-$\underline{C}$), 29.0 (s, Cy-$\underline{C}$), 34.9 (s, Cy-$\underline{C}$)

IR (KBr): ν[cm$^{-1}$]=2921 (s) 2854 (s), 2358 (w), 1449 (m), 1326 (w), 1294 (w), 1264 (w), 1204 (w), 1179 (w), 1111 (w), 1069 (m), 1046 (w), 1026 (w), 996 (w), 915 (w), 885 (w), 850 (w), 820 (w), 774 (w), 746 (w), 708 (w), 684 (w), 655 (w), 530 (w), 510 (w), 462 (w)

20 MS (LT-FAB$^+$): m/e=536 [M]$^+$ (correct isotope pattern), 501 [M-Cl]$^+$ (correct isotope pattern)

1.3.2. Synthesis of dibenzyl[bis(dicyclohexylphosphino)methane-κ$^2$P] nickel (II), (dcpm-κ$^2$P)NiBn$_2$ 200 mg (0.37 mmol) of (dcpm-κ$^2$P)NiCl$_2$ were suspended in pentane. At room temperature, 0.74 ml (0.74 mmol) of a solution of PhCH$_2$MgCl (1M in diethyl ether) were added. After 30 minutes, the solution became reddish. To remove the magnesium chloride formed, the product was taken up in toluene and filtered through Celite®.

Yield: 175.2 mg (73%)

Elemental analysis for $C_{39}H_{60}P_2Ni$:

calculated: C, 72.12; H, 9.31; P, 9.54.

found: C, 72.29; H, 9.48; P, 9.39.

Melting point: 96° C. (decomposition)

$^1$H-NMR spectrum (500 MHz, $C_6D_6$, T=298 K): δ=1.16 (quintet, $^3J_{HH}$=9.00 Hz, 16H, Cy-H), 1.36 (t, $^3J_{HH}$=11.50 Hz, 8H, Cy-H), 1.74 (quintet, $^3J_{HH}$=7.00 Hz, 16 H, Cy-H), 2.10 (d, $^2J_{PH}$=11.75 Hz, 6H, Cy-H), 2.69 (s, 4 H, C$\underline{H}_2$—Ph), 7.04 (t, $^3J_{HH}$=7.35 Hz, 2 H, C$_{para}$—H), 7.24 (t, $^3J_{HH}$=7.70 Hz, 4 H, C$_{meta}$—H), 7.49 (d, $^3J_{HH}$=7.70 Hz, 4 H, C$_{ortho}$—H)

$^{31}$P-NMR spectrum (122 MHz, $C_6D_6$, T=298 K): δ=−4.13 s $^{13}$C-NMR (126 MHz, $C_6D_6$, T=298 K): δ=17.03 (t, $^1J_{PC}$=14.1 Hz, P—$\underline{C}H_2$—P), 26.73 (s, Cy-C), 27.59 (s, Cy-C), 27.80 (m, Cy-C), 29.28 (s, Cy-C), 30.41 (Cy-C), 34.83 (m, P—$\underline{C}$H), 120.95 (s, o-C benzyl), 128.94 (s, m-C benzyl), 129.47 (s, p-C benzyl), 155.35 (s, i-C benzyl)

IR (KBr): ν[cm$^{-1}$]=3061 (w), 3027 (w), 2927 (s), 2825 (m), 2361 (s), 2342 (m), 1449 (w), 1262 (m), 1217 (w), 1161 (m), 1098 (s), 1022 (s), 889 (w), 855 (w), 800 (s), 698 (m), 669 (w)

MS (LT-FAB$^+$): m/e=557 [M+H-toluene]$^+$ with correct isotope pattern 1.3.3. Synthesis of (η$^3$-benzyl) [bis(dicyclohexylphosphino)methane-κ$^2$P] nickel (II)-tetrakis[3,5-bis(trifluoromethyl)phenyl]borate,

[(dcpm-κ$^2$P)Ni(η$^3$—CH$_2$Ph]$^+$[B(C$_6$H$_3$\{CF$_3$\}$_2$)$_4$]$^-$ 20 mg (30.8 μmol) of (dcpm-κ$^2$P)NiBn$_2$ were suspended in 10 ml of diethyl ether and cooled to −60° C. 31.2 mg (30.8 mol) of [H(OEt$_2$)$_2$][B(C$_6$H$_3$\{CF$_3$\}$_2$)$_4$] were dissolved in 5 ml of diethyl ether and added to the suspension at −60° C. The solution was slowly warmed to room temperature. After 24 hours at room temperature, the solution has become orange. The product was crystallized by addition of pentane. It was recrystallized once from ether/pentane.

Yield: 24 mg (55%)

Melting point: 167° C. (decomposition)

Elemental analysis for $C_{64}H_{65}P_2F_{24}BNi$:

calculated: C, 54.07; H, 4.61; P, 4.36.

found: C, 53.86; H, 4.96; P, 4.38.

$^1$H-NMR spectrum (500 MHz, $CD_2Cl_2$, T=298 K): δ=1.0–2.1 (9 m, 44 H, Cy-H), 2.30 (d, $^3J_{PH}$=4.7 Hz, 2 H, C$\underline{H}_2$—Ph), 2.59 (t, $^2J_{PH}$=9.0 Hz, 2 H, P—C$\underline{H}_2$—P), 6.33 (d, $^3J_{HH}$=7.3 Hz, 2 H, o-H benzyl), 7.30 (m, 1 H, p-H benzyl), 7.56 (s, 4 H, p-H [B(C$_6$H$_3$\{CF$_3$\}$_2$)$_4$]), 7.61 (t, $^3J_{HH}$=7.7 Hz, 2 H, m-H benzyl), 7.72 (s, 8 H, o-H [B(C$_6$H$_3$\{CF$_3$\}$_2$)$_4$])

$^{31}$P-NMR (122 MHz, d$_6$-acetone, T=298 K): δ=−3.5 (d, $^2J_{PP}$=37.9 Hz), 12.6 (d, $^2J_{PP}$=37.9 Hz)

13C-NMR (75 MHz, d$_6$-acetone, T=298 K): δ=19.56 (t, $^1J_{PC}$=20.9 Hz, P—$\underline{C}H_2$—P), 25.20 (s, Cy-$\underline{C}$), 25.34 (Cy-$\underline{C}$), 26.40 (m, 2 Cy-$\underline{C}$), 28.55 (m, 2 Cy-$\underline{C}$), 33.80 (dd, $^1J_{PC}$=12.6 Hz, 3J$_{PC}$=4.4 Hz, $\underline{C}$1Cy), 34.94 (dd, $^2J_{PC}$=24.7 Hz, $^2J_{PC}$=3.3 Hz, $\underline{C}H_2$-benzyl), 35.45 (dd, $^1J_{PC}$=16.5 Hz, $^3J_{PC}$=5.5 Hz, $\underline{C}$1Cy), 112.22 (d, $^2J_{PC}$=7.7 Hz, o-C benzyl), 117.12 (m, i-C benzyl), 117.45 (m, p-C [B(C$_6$H$_3$\{CF$_3$\}$_2$)$_4$]), 126.82 (m, p-C benzyl), 134.57 (s, o-C [B(C$_6$H$_3$\{CF$_3$\}$_2$)$_4$]), 135.68 (s, m-C benzyl)

Synthesis Example 1.4:

Synthesis of (η$^3$-benzyl) [bis(dicyclohexylphosphino)methane-κ$^2$P] nickel (II) tetrafluoroborate [(dcpm-κ$^2$P)Ni (η$^3$—CH$_2$Ph]$^+$[BF$_4$]$^-$ (formula 4)

10.4 mg (16.0 μmol) of (dcpm-κ$^2$P)NiBn$_2$ (preparation as in example 1.3.2.) were suspended in 3 ml of diethyl ether, after which 2.2 μl of a 54% solution of HBF$_4$ in ether were added. After 24 hours, a light-orange precipitate had formed and the solution was pale yellow. The solution was siphoned off and the precipitate was washed once with 1 ml of pentane.

Drying in a high vacuum gave 8.5 mg (82%) of product.

For monitoring the reaction, the product was taken up in d$_8$-THF and the NMR spectrum was determined.

2. Polymerisation Examples

The order of the polymerization examples corresponds to the order of the polymerizations The inonic metal compounds from synthesis examples 1.1 to 1.3 were weighed into a 10 ml glass autoclave. 5 ml of diethyl ether were added and the solution was brought to the desired temperature (a water bath was used for removal of heat). The autoclave was flushed a number of times with ethylene and placed under an ethylene pressure of 5 bar.

After the polymerization reaction, the autoclave was vented and the polymer was filtered off. The polymer was washed a number of times with diethyl ether and acetone and dried at 70° C.

The ionic metal compound from synthesis example 1.4. was processed as follows:

The solution obtained from the NMR examination was diluted with 5 ml of methylene chloride and introduced into the glass autoclave. 10 bar of ethylene were injected at room temperature and polymerization was carried out for 24 hours. Further ethylene was introduced to maintain the pressure, but the pressure fluctuated between 8 and 10 bar.

The polymer was worked up by repeated washing with acetone and drying at 70° C.

Yield: 530 mg

TABLE 1

| No. | Ionic metal compound | Weight used [mg] | [μmol] | T [° C.] | Pressure [bar] | t [h] | PE [mg] |
|---|---|---|---|---|---|---|---|
| 1a | (dtbpm)-Nistilbeneyl+ [B (C6H3 {CF3}2)4]− | 18.6 | 12 | 44 | 7 | 3 | 665 mg |
| 2a | (dtbpm)NiBn+ [B (C6H3 {CF3}2)4]− | 3.3 | 2.5 | 40 | 10 | 6 | 84 mg |
| 3a | (dcpm)NiBn+ [B (C6H3 {CF3}2)4]− | 7.4 | 5.2 | 40 | 10 | 3.5 | 129 mg |
| 4a | (dcpm) NiBn+BF4− | 8.5 | 13.2 | 25 | 10 | 24 | 530 mg |

3. Polymer Analisis

The polymerizations with the aid of the benzyl complexes, whose analytical data are shown below, were carried out at room temperature. The procedure otherwise corresponded to the method described above.

The content and substitution pattern of the double bonds were determined by IR spectroscopy, and the molecular weights of the polyethylenes were determined by GPC. The polymer viscosity was determined in accordance with ISO 1628-3. The results are summarized in table 2.

TABLE 2

| Example | 1b (dtbpm) NiBn+ | 2b (dtbpm) Ni(1-benzyl)-benzyl+ | 3b (dcpm) NiBn+ |
|---|---|---|---|
| h (dl/g) | 2.25 | 2.53 | 0.36 |
| $M_w$ (g/mol) | 167 917 | 182 137 | 10 825 |
| $M_n$ (g/mol) | 59 110 | 73 590 | 3365 |
| Q | 2.84 | 2.48 | 3.22 |
| M.p. [° C.] | 134.9 | n.d. | 124 |
| Trans-vinylene (1/1000) | 0.19 | 0.07 | 0.23 |
| Vinyl (1/1000) | 0.12 | 0.05 | 3.11 |
| Vinylidene (1/1000) | 0.06 | 0.08 | 0.49 |
| Total CH3, (1/1000) | 1 | 1 | 6 |

Q: Polydispersity

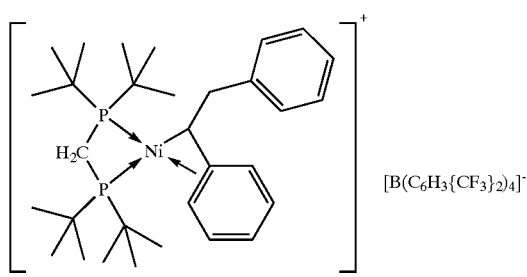

1

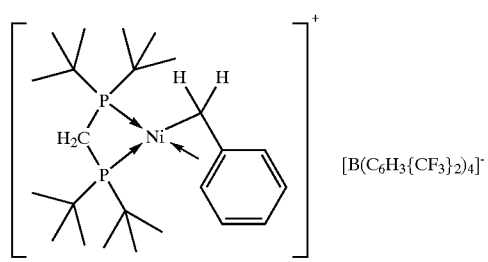

2

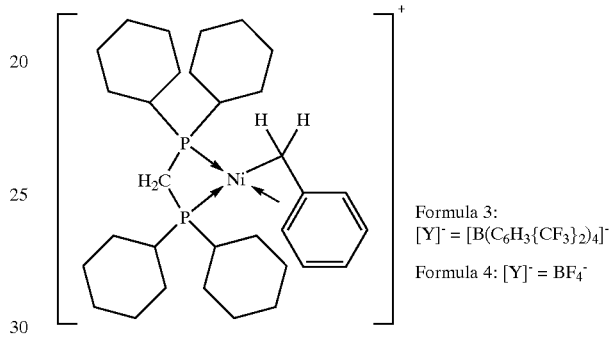

Formula 3: [Y]− = [B(C6H3{CF3}2)4]−

Formula 4: [Y]− = BF4−

We claim:
1. A metal compound of the formula I,

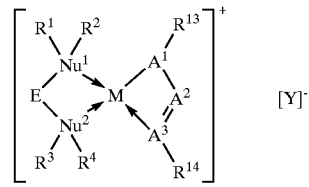

I where the variables are defined as follows:
 M is Ni in the oxidation state +II;
 $Nu^1$, $Nu^2$ are each P,
 E is

and
 $E^1$, is selected from among C, Si and Ge;
 $R^1$ to $R^6$ are selected independently from among
  hydrogen,
  $C_1$–$C_8$-alkyl, substituted or unsubstituted,
  $C_2$–$C_8$-alkenyl, substituted or unsubstituted, having from one to 4 isolated or conjugated double bonds;
  $C_3$–$C_{12}$-cycloalkyl, substituted or unsubstituted,
  $C_7$–$C_{13}$-aralkyl,
  $C_6$–$C_{14}$-aryl, unsubstituted or monosubstituted or polysubstituted by identical or different substituents selected from among
   $C_1$–$C_8$-alkyl, substituted or unsubstituted,
   $C_3$–$C_{12}$-cycloalkyl, $C_7$–$C_{13}$-aralkyl,
$C_6$–$C_{14}$-aryl,
halogen,
$C_1$–$C_6$-alkoxy, substituted or unsubstituted,
$C_6$–$C_{14}$-aryloxy,
$SiR^{18}R^{19}R^{20}$ and $O—SiR^{18}R^{19}R^{20}$, where $R^{18}$–$R^{20}$ are selected from among hydrogen, $C_1$–$C_8$-alkyl, $C_3$–$C_{12}$-cycloalkyl, $C_7$–$C_{13}$-aralkyl and $C_6$–$C_{14}$-aryl;
five- to six-membered nitrogen-containing heteroaryl radicals, unsubstituted or monosubstituted or polysubstituted by identical or different substituents selected from among
$C_1$–$C_8$-alkyl, substituted or unsubstituted,
$C_3$–$C_{12}$-cycloalkyl,
$C_7$–$C_{13}$-aralkyl,
$C_6$–$C_{14}$-aryl,
halogen,
$C_1$–$C_6$-alkoxy,
$C_6$–$C_{14}$-aryloxy,
$SiR^{18}R^{19}R^{20}$ and $O—SiR^{18}R^{19}R^{20}$, where $R^{18}$–$R^{20}$ are selected from among hydrogen, $C_1$–$C_8$-alkyl, $C_3$–$C_{12}$-cycloalkyl, $C_7$–$C_{13}$-aralkyl and $C_6$–$C_{14}$-aryl;
where adjacent radicals $R^1$ to $R^6$ together with E may be joined to form a saturated or olefinically unsaturated 5- to 12-membered ring;
$A^1$, $A^3$ are selected from among $C—R^{15}$, $C—R^{16}$, $Si—R^{15}$, $Si—R^{16}$ and N,
$A^2$ is selected from among $C—R^{17}$, $Si—R^{17}$ and N, where not more than one $A^j$ is a nitrogen atom and $j=1,2,3$;
$R^{13}$ to $R^{17}$ are selected from among
hydrogen,
$C_1$–$C_8$-alkyl, substituted or unsubstituted,
$C_2$–$C_8$-alkenyl, substituted or unsubstituted, having from one to 4 isolated or conjugated double bonds;
$C_3$–$C_{12}$-cycloalkyl, substituted or unsubstituted,
$C_7$–$C_{13}$-aralkyl,
$C_6$–$C_{14}$-aryl, unsubstituted or monosubstituted or polysubstituted by identical or different substituents selected from among
$C_1$–$C_8$-alkyl, substituted or unsubstituted,
$C_3$–$C_{12}$-cycloalkyl,
$C_7$–$C_{13}$-aralkyl,
$C_6$–$C_{14}$-aryl,
halogen,
$C_1$–$C_6$-alkoxy,
$C_6$–$C_{14}$-aryloxy,
$SiR^{18}R^{19}R^{20}$ and $O—SiR^{18}R^{19}R^{20}$, where $R^{18}$–$R^{20}$ are selected from among hydrogen, $C_1$–$C_8$-alkyl, $C_3$–$C_{12}$-cycloalkyl, $C_7$–$C_{13}$-aralkyl and $C_6$–$C_{14}$-aryl;
five- to six-membered nitrogen-containing heteroaryl radicals, unsubstituted or monosubstituted or polysubstituted by identical or different substituents selected from among
$C_1$–$C_8$-alkyl, substituted or unsubstituted,
$C_3$–$C_{12}$-cycloalkyl,
$C_7$–$C_{13}$-aralkyl,
$C_6$–$C_{14}$-aryl,
halogen,
$C_1$–$C_6$-alkoxy,
$C_6$–$C_{14}$-aryloxy,
$SiR^{18}R^{19}R^{20}$ and $O—SiR^{18}R^{19}R^{20}$, where $R^{18}$–$R^{20}$ are selected from among $C_1$–$C_8$-alkyl, $C_3$–$C_{12}$-cycloalkyl, $C_7$–$C_{13}$-aralkyl and $C_6$–$C_{14}$-aryl;
where $R^{13}$ to $R^{17}$ together with one or more atoms $A^j$ may form a saturated or unsaturated 5- to 12-membered ring, and $[Y]^-$ is an anion.

2. A metal compound as claimed in claim 1 in which $E^1$ is carbon and $R^1$ is identical to $R^2$, $R^3$ is identical to $R^4$ and $R^5$ is identical to $R^6$.

3. A metal compound as claimed in any of claim 1 in which the variables are defined as follows:
$[Y]^-$ is selected from among $BF_4^-$, $[BAr_4]^-$, $PF_6^-$, $AsF_6^-$, $SbF_6^-$, $ClO_4^-$, $CF_3SO_2^-$ and $CF_3CO_2^-$, where
Ar are $C_6$–$C_{14}$-aromatic radicals which may be identical or different and may be monosubstituted or polysubstituted by halogen, $C_1$–$C_8$-alkyl or $C_6$–$C_{14}$-aryl which may in turn be monosubstituted or polysubstituted by halogen or CN; $R^1$ to $R^6$ are selected from among hydrogen, $C_1$–$C_8$-alkyl, substituted or unsubstituted, $C_2$–$C_8$-alkenyl, substituted or unsubstituted, having from one to 4 isolated or conjugated double bonds; $C_6$–$C_{14}$-aryl, unsubstituted or monosubstituted or polysubstituted by identical or different, substituted or unsubstituted $C_1$–$C_8$-alkyl groups,
where adjacent radicals $R^1$ to $R^6$ together with E may be joined to form a saturated or unsaturated 5- to 12-membered ring;
$A^1$, $A^3$ are selected from among $C—R^{15}$, $C—R^{16}$, $Si—R^{15}$ and $Si—R^{16}$,
$A^2$ is selected from among $C—R^{17}$ and $Si—R^{17}$,
$R^{13}$ to $R^{17}$ are selected from among
hydrogen,
$C_1$–$C_8$-alkyl, substituted or unsubstituted,
$C_2$–$C_8$-alkenyl, substituted or unsubstituted, having from one to 4 isolated or conjugated double bonds;
$C_3$–$C_{12}$-cycloalkyl, substituted or unsubstituted,
$C_7$–$C_{13}$-aralkyl,
$C_6$–$C_{14}$-aryl, unsubstituted or monosubstituted or polysubstituted by identical or different, substituted or unsubstituted $C_1$–$C_8$-alkyl groups,
where $R^{13}$ to $R^{17}$ together with one or more atoms $A^j$ may form a saturated or unsaturated 5- to 12-membered ring.

4. A metal compound as claimed in claim 1 in which $BF_4^-$ is present as anion and the variables are defined as follows:
$R^1$ to $R^4$ are each tert-butyl or cyclohexyl,
$R^5$, $R^6$, $R^{13}$ are each hydrogen,
$A^1$, $A^2$, $A^3$ are each C—H.

5. A metal compound as claimed in claim 1 in which $BF_4^-$ is present as anion and the variables are defined as follows:
$R^1$ to $R^4$ are each tert-butyl or cyclohexyl,
$R^5$, $R^6$, $R^{13}$ are each hydrogen,
$A^1$, $A^3$ are each C—H,
$A^2$ is $C—R^{17}$, and $R^{14}$ and $R^{17}$ together form a 1,3-butadiene-1,4-diyl unit.

6. A process comprising polymerization or copolymerization of olefins with a metal compound as claimed in claim 1.

7. A process for preparing a supported catalyst for the polymerization or copolymerization of olefins comprising deposition of one or more metal compounds as claimed in any of claim 1 on a solid support material.

8. A supported catalyst for the polymerization or copolymerization of olefins made by the process of claim 7.

9. A process for the polymerization or copolymerization of olefins in bulk, in the gas phase or in suspension using a supported catalyst as claimed in claim 8.

10. A process for preparing an ionic metal compound as claimed in claim 1, which comprises reacting a metal complex of the formula II,

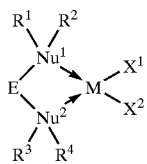

II where $X^1$ and $X^2$ are each halogen, with two equivalents of a compound of the formula III a

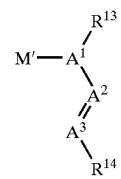

III a

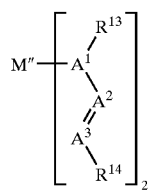

III b or at least one equivalent of a compound of the formula III b
where the variables are defined as follows:
M' is selected from among Li, Na, K, Rb, Cs and $MgX^3$;
M" is selected from among Mg and Ca,
$X^3$ is selected from among chlorine, bromine and iodine;
and subsequently adding one equivalent of a derivative of the anion $[Y]^-$ to eliminate one equivalent of the anion of the compound III, where either the acid H—Y or salts of $[Y]^-$ with Brønsted-acid cations are used as derivative of the anion $[Y]^-$.

11. A process as claimed in claim 10, wherein oxonium ions or ammonium ions are used as Brønsted-acid cations.

12. A metal compound as claimed in claim 1, which has the following formula IV:

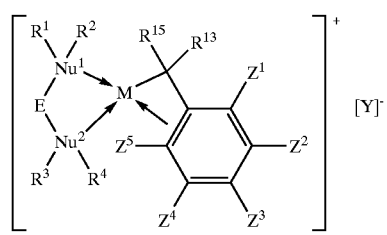

IV wherein $Z^1$ to $Z^5$ are identical or different and are selected from among hydrogen, substituted and unsubstituted $C_1$–$C_8$-alkyl, substituted and unsubstituted $C_2$–$C_8$-alkenyl, substituted and unsubstituted $C_3$–$C_{12}$-cycloalkyl, $NO_2$, halogen, $C_7$–$C_{13}$-arylalkyl, $C_6$–$C_{14}$-aryl, and wherein two adjacent radicals $Z^1$ to $Z^5$ together with a phenyl may form a 5- to 12-membered ring.

13. A process comprising polymerization or copolymerization of olefins with a metal compound as claimed in claim 12.

14. A process for preparing a supported catalyst for the polymerization or copolymerization of olefins comprising deposition of one or more metal compounds as claimed in claim 12 on a solid support material.

15. A supported catalyst for the polymerization or copolymerization of olefins made by the process of claim 14.

16. A process for the polymerization or copolymerization of olefins in bulk, in the gas phase or in suspension using a supported catalyst as claimed in claim 15.

* * * * *